(12) United States Patent
Gabetta et al.

(10) Patent No.: US 8,013,151 B2
(45) Date of Patent: Sep. 6, 2011

(54) PROCESS FOR THE PREPARATION OF GALANTHAMINE HYDROBROMIDE

(75) Inventors: Bruno Gabetta, Milan (IT); Enrico Mercalli, Milan (IT)

(73) Assignee: Indena S.p.A., Milan (IT)

( * ) Notice: Subject to any disclaimer, the term of this patent is extended or adjusted under 35 U.S.C. 154(b) by 826 days.

(21) Appl. No.: 11/793,097

(22) PCT Filed: Nov. 23, 2005

(86) PCT No.: PCT/EP2005/012521
§ 371 (c)(1),
(2), (4) Date: Mar. 6, 2008

(87) PCT Pub. No.: WO2006/063666
PCT Pub. Date: Jun. 22, 2006

(65) Prior Publication Data
US 2009/0043092 A1 Feb. 12, 2009

(30) Foreign Application Priority Data
Dec. 17, 2004 (IT) .............................. MI2004A2413

(51) Int. Cl.
*C07D 491/10* (2006.01)
(52) U.S. Cl. ...................................................... 540/576
(58) Field of Classification Search .................... 540/576
See application file for complete search history.

(56) References Cited

U.S. PATENT DOCUMENTS

| 2002/0028802 A1 | 3/2002 | Hille et al. ............... 514/213.01 |
| 2003/0092700 A1 | 5/2003 | Czollner et al. ......... 514/217.01 |

FOREIGN PATENT DOCUMENTS

| GB | 938 767 | 10/1963 |
| GB | 942 200 | 11/1963 |

OTHER PUBLICATIONS

Han et al., "Chemical and Pharmacological Characterization of Galanthamine, an Acetylcholinesterase Inhibitor, and its Derivatives. A Potential Application in Alzheimer's Disease?", Eur J Med 27(7)673-687, 1992.
Chemical Abstracts Service, Columbus, Ohio, US, Zheng et al., "Method for Separation of High-Purity Galanthamine from Lycoris Radiata Crude Extract", XP002336902, Retrieved from STN Database Accession No. 2005:401473 Abstract & CN 1490 319 CN (Yixin Pharmaceutical Co., Ltd. Zhejiang Prov. Peop. Rep. China) Jul. 28, 2003.

*Primary Examiner* — Brenda Coleman
(74) *Attorney, Agent, or Firm* — Porzio, Bromberg & Newman, P.C.

(57) ABSTRACT

A process for the purification of galanthamine (I) comprising precipitation of galanthamine hydrobromide from a mixture of alkaloids obtained from a plant of the Amaryllidaceae family containing galanthamine, treatment of the hydrobromide with alkali, extraction and crystallization of galanthamine with a solvent of general formula (II), in which $R_1$ is hydrogen or methyl and $R_2$ is selected from n-butyl, isobutyl, sec-butyl and t-butyl. The resulting pure galanthamine can be conveniently used for the preparation of galanthamine hydrobromide.

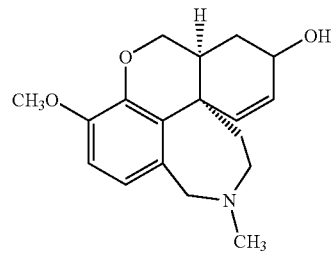

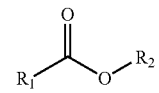

12 Claims, No Drawings

PROCESS FOR THE PREPARATION OF GALANTHAMINE HYDROBROMIDE

This application is a national stage entry under 35 U.S.C. §371 of PCT/EP2005/012521, filed Nov. 23, 2005.

FIELD OF THE INVENTION

The invention relates to the purification of tetracyclic alkaloids, in particular to the purification of galanthamine.

BACKGROUND OF THE INVENTION

Galanthamine, ((−)-[4aS-(4aα,6β,8aR)]-4a,5,9,10,11,12-hexahydro-3-methoxy-11-methyl-6H-benzofuro[3a,3,2,-ef][2]benzazepine-6-ol) (I),

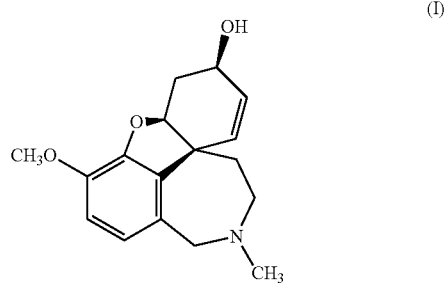

is a tetracylic alkaloid which reversibly inhibits cholinesterase. Its effects are similar to those of physostigmine and neostigmine, but its inhibitory effect is lower. However, this drawback is counterbalanced by a broader therapeutical spectrum and lower toxicity. Galanthamine is used for the treatment of narrow-angle glaucoma, intoxications, nicotine and alcohol dependency and different pathologies of the nervous system, such as the Alzheimer's syndrome. For clinical purposes, it is administered in the form of hydrobromide, whose preparation was first described in the fifties (N. F. Proskumina et al., Zhur. Obshchei Khim. 22, 1899 (1952)).

Galanthamine can be prepared by total synthesis, but due to the presence of three chiral centres, the methodologies are particularly complicated. More commonly, galanthamine is isolated from plants of the Amaryllidaceae family, for example plants of the genus *Galanthus, Crinum, Leucojum* and *Narcissus*, which also contain several galanthamine-related compounds. In these plants galanthamine can be present in traces or in the maximum amount of 0.3%. However, many of these plants are protected species and therefore the recovery of galanthamine on an industrial scale requires the use of biomasses obtained from cultivations.

The presence of a relevant number of galanthamine structurally-related compounds makes it troublesome and often expensive to recover galanthamine in a purity suitable for the pharmaceutical use, in particular for the preparation of galanthamine hydrobromide.

The preparation of mixtures of galanthamine and related compounds from plant materials is generally carried out using conventional methods for the extraction of alkaloids, which comprise wetting the plant material with alkali solutions suitable for hydrolysing the alkaloid salts contained in the biomass to free bases and extracting with solvents wherein the alkaloid bases are soluble.

In the particular case of galanthamine-containing plants, the alkali solutions are solutions of inorganic bases such as sodium, calcium, potassium hydroxide or carbonate or solutions of ammonium hydroxide. Water-miscible solvents such as methanol, ethanol and acetone, or water-immiscible solvents, such as aliphatic and aromatic hydrocarbons or esters, for example ethyl acetate, can be used as extraction solvents. Extractions can be carried out at temperatures ranging from 20° C. to the boiling temperature of the solvent. Preferably, concentrated aqueous solutions of sodium carbonate can be used for the hydrolysis of the alkaloid bases; for the extractions, toluene at temperatures ranging from 20 to 70° C. can be used. With respect to the other solvents mentioned above, toluene has the advantage of satisfactorily exhausting the alkaloids while avoiding the extraction of polar constituents which would make the subsequent purification steps troublesome.

The alkaloids contained in the toluene extracts can be separated from the non-alkaloid components by extraction with an acidic aqueous solution, for example a 2% sulfuric acid solution, followed by alkalinization with sodium or potassium hydroxide, or sodium or potassium carbonate and single re-extraction with toluene, whereby the alkaloid components are obtained as a mixture.

These procedures allow to obtain from Amaryllidaceae complex mixtures of alkaloids having a galanthamine content ranging from 30 to 40%. There is still therefore the need for a purification process which provides galanthamine suitable for pharmaceutical use.

DETAILED DESCRIPTION OF THE INVENTION

It has now been found that highly pure galanthamine for pharmaceutical use can be obtained precipitating galanthamine (I)

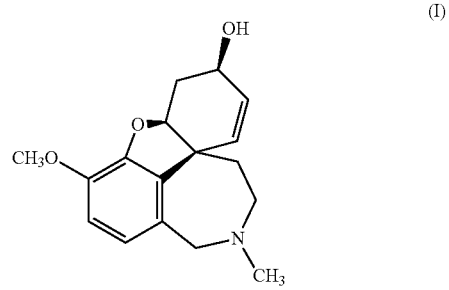

as hydrobromide from an alkaloids mixture containing galanthamine obtained from a plant belonging to the Amaryllidaceae family, hydrolysing the hydrobromide and extracting galanthamine with a suitable solvent.

In particular, the invention relates to a process comprising the following steps:
a) addition of hydrobromic acid to a mixture of alkaloids containing galanthamine obtained from a plant of the Amaryllidaceae family;
b) recovery of the precipitate;
c) dissolution of the precipitate in a basic aqueous solution;
d) extraction with a solvent of general formula (II)

in which $R_1$ is hydrogen or methyl and $R_2$ is selected from n-butyl, isobutyl, sec-butyl and tert-butyl;
e) concentration of the organic phase;
f) optional recovery of the precipitated galanthamine (I).

The preparation of the alkaloids mixture can be carried out according to conventional methods, for example according to what described in the background of the invention.

The precipitation of galanthamine hydrobromide from the alkaloids mixture is carried out preferably with aqueous hydrobromic acid in an alcoholic solvent, for example in methanol, ethanol, propanol or iso-propanol, preferably ethanol. The salification is carried out keeping the temperature from −20 to 20° C., preferably from 0 to 5° C. during the addition of hydrobromic acid, using 5 to 7 volumes of solvent compared with the weight of the alkaloids mixture and a 5-10% excess of hydrobromic acid to the stoichiometric amount, assuming that the alkaloids have the same molecular weight as galanthamine (287 m.u.).

The precipitation of galanthamine hydrobromide allows to increase the purity from 30-40% to 85-90%, with substantially quantitative recovery, since the mother liquors contain only traces of galanthamine hydrobromide.

The alkali aqueous solutions used for dissolving the precipitate, i.e. to hydrolyse galanthamine from the hydrobromide salt, are preferably aqueous solutions at pH≧8, containing for example sodium carbonate, potassium carbonate or ammonium hydroxide.

Even if the solvents of general formula (II) used for the extraction and precipitation of galanthamine base are not frequently used for the extraction and especially for the crystallization of alkaloids, they give surprisingly good results in the extraction and crystallization of galanthamine. A preferred solvent is n-butyl acetate; after extraction the organic phase is concentrated under vacuum until incipient crystallization.

After filtration galanthamine sufficiently pure for conversion to hydrobromide for the pharmaceutical use is obtained in 85% yield.

The preparation of galanthamine hydrobromide from galanthamine obtained according to the process of the present invention can be carried out with conventional methods generally used for the salification of alkaloids.

For this purpose, galanthamine is dissolved in a suitable solvent, preferably acetone, or an alcohol, preferably 95% ethanol, and added at 0 to 5° C. with a stoichiometric amount of aqueous hydrobromic acid. According to a particularly preferred embodiment of the invention, the hydrobromide can be prepared without isolating galanthamine. After extraction with n-butyl acetate the combined organic extracts are concentrated to about 1/16 of the volume, then the solvent and hydrobromic acid are added as described above. After filtration and crystallization from water, galanthamine hydrobromide is obtained with purity higher than 99%, the content of each impurity being lower than 0.1%. The product is therefore suitable for pharmaceutical use.

The following examples illustrate the invention in greater detail.

EXAMPLES

Example 1

Preparation of a Mixture of Alkaloids from *Narcissus Pseudonarcissus* "Carlton" Bulbs Ground vegetable material (500 kg) containing 0.3% galanthamine is added with 850 l of 10% w/v aqueous sodium carbonate and extracted with 7×1000 l toluene operating at 65-70° C.

The extracts are combined and concentrated under vacuum to a volume of 300 l. The concentrated solution is treated with 50 l of 2% sulfuric acid and the aqueous phase is collected. The aqueous phase is adjusted to pH 9 by addition of ammonium hydroxide and the resulting solution is extracted with 4×50 l of toluene. The combined organic phases are concentrated to dryness under vacuum. 3.5 kg of total alkaloids are obtained containing 40% galanthamine (HPLC analysis).

Example 2

Preparation of Galanthamine by Crystallization from N-Butyl Acetate

Total alkaloids (3.5 kg) containing 40% galanthamine, obtained according to example 1, are dissolved in 20 l of 95% ethanol. The solution is cooled to 0° C. and added under stirring with 2.1 l of 48% aqueous hydrobromic acid, keeping the temperature during the addition between 0 and 5° C. The mixture is left under stirring at room temperature for four hours, the product is recovered by filtration, washed with 95% ethanol and dried under vacuum at 60° C. 2.22 kg of galanthamine hydrobromide having HPLC purity of 88% are obtained. The filtration mother liquors, which contain traces of galanthamine hydrobromide, are removed.

The resulting 88% galanthamine hydrobromide is suspended in 7.6 l of water. The suspension is cooled to 0° C. and diluted, keeping the temperature from 0 to 5° C., with 5.2 l of 10% sodium carbonate. Five extractions with 5 l of n-butyl acetate are obtained, the organic phases are pooled and washed with 2.5 l of salted water. The organic phases are concentrated under vacuum to a volume of 4 l and allowed to crystallize at room temperature. The crystals are filtered and dried under vacuum at 70° C. 1.2 kg of galanthamine are obtained with chemical-physical and spectroscopical characteristics consistent with those reported in the literature (P. Carroll et al., *Bull. Soc. Chim. Fr.* (1990), 127, 769).

Example 3

Preparation of Galanthamine by Crystallization from T-Butyl Acetate

Total alkaloids (3.5 kg) containing 40% galanthamine, obtained according to example 1, are dissolved in 24 l of isopropanol. The solution, cooled to 0° C., is treated under stirring with 2.1 l of 48% aqueous hydrobromic acid, keeping the temperature during the addition between 0 and 5° C. The mixture is left under stirring at room temperature for three hours, then filtered and the solid is washed with some isopropanol and dried under vacuum at 70° C. 2.28 kg of galanthamine hydrobromide having HPLC purity of 85% are obtained. The resulting solid is suspended in 8 l of water, cooled to 0° C. and diluted with 5.5 l of 10% sodium carbonate. Seven extractions with 5 l of t-butyl acetate are carried out.

The organic phases are pooled, washed with 3 l of salted water and concentrated under vacuum to 4.4 l, then left to crystallize at room temperature. The resulting crystals are filtered and dried under vacuum at 70° C. 1.25 kg of galanthamine having the same quality as that of example 2 are obtained.

Example 4

Preparation of Galanthamine Hydrobromide Having a Purity not Lower than 99%

Galanthamine obtained according to examples 2 and 3 (1.64 kg) is dissolved in 11.5 l of 95% ethanol. The solution is cooled to 0° C. and treated under stirring with 0.76 l of 48% hydrobromic acid, keeping the temperature at 0-5° C. during the addition.

The mixture is left to stand for four hours and filtered, washing the precipitate with 1.5 l of 95% ethanol. The wet solid is dissolved at 50° C. in 18 l of 30% aqueous ethanol and the solution is concentrated under vacuum to a volume of 6 l and left to crystallize overnight. The crystallized solid is filtered, washed with 1.9 l of water and dried under vacuum at 50° C. 1.9 kg of galanthamine hydrobromide having HPLC purity higher than 99% are obtained, each impurity being lower than 0.1%.

Example 5

Preparation of Galanthamine Hydrobromide Having Purity not Lower than 99%

Total alkaloids (3.5 kg) containing 40% galanthamine, obtained according to example 1, are dissolved in 20 l of 95% ethanol. The solution is cooled to 0° C. and treated under stirring with 2.1 l of 48% aqueous hydrobromic acid, keeping the temperature during the addition between 0 and 5° C. The mixture is left under stirring at room temperature for four hours, the product is collected by filtration, washed with 95% ethanol and dried under vacuum at 60° C. 2.22 kg of galanthamine hydrobromide are obtained having HPLC purity of 88%. The mother liquors from filtration, which contain traces of galanthamine hydrobromide, are removed.

The resulting 88% galanthamine hydrobromide is suspended in 7.6 l of water. The suspension is cooled to 0° C. and diluted with 5.2 l of 10% sodium carbonate, keeping the temperature from 0 to 5° C. and extracted with 5×5 l of n-butyl-acetate. The organic phases are pooled, washed with 2.5 l of salted water, concentrated under vacuum to a volume of 1.6 l and then added with 8.4 l of 95% ethanol. The solution is cooled to 0° C. and added under stirring with 0.56 l of 48% hydrobromic acid, keeping the temperature at 0-5° C.

The mixture is allowed to stand for four hours and filtered, washing the precipitate with 1.1 l of 95% ethanol. The wet solid is dissolved at 50° C. in 13.2 l of 30% aqueous ethanol, the solution is concentrated under vacuum to a volume of 4.4 l and left to crystallize overnight. The resulting crystals are filtered, washed with 1.4 l of water and dried under vacuum at 50° C. 1.4 kg of galanthamine hydrobromide having HPLC purity higher than 99% is obtained, each impurity being lower than 0.1%.

The invention claimed is:

1. A process for the purification of galanthamine (I)

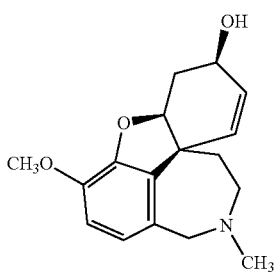

comprising the following steps:
 a) addition of hydrobromic acid to a mixture of alkaloids containing galanthamine obtained from a plant of the Amaryllidaceae family;
 b) recovery of the precipitate;
 c) dissolution of the precipitate in a basic aqueous solution;
 d) extraction with a solvent of formula (II)

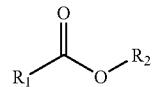

in which $R_1$ is hydrogen or methyl and $R_2$ is selected from n-butyl, isobutyl, sec-butyl and t-butyl;
 e) concentration of the organic phase;
 f) optional recovery of the precipitated galanthamine (I).

2. The process as claimed in claim 1 wherein the mixture of alkaloids is dissolved in a solvent selected from methanol, ethanol, propanol or isopropanol.

3. The process as claimed in claim 2 in which the solvent is ethanol.

4. The process as claimed in claim 2 in which the solvent is added in amounts ranging from 5 to 7 volumes on the weight of the mixture of alkaloids.

5. The process according to claim 2 in which hydrobromic acid is added as aqueous hydrobromic acid.

6. The process according to claim 2 in which the addition is carried out at a temperature ranging from −20 to 20° C.

7. The process as claimed in claim 6 in which the temperature ranges from 0 to 5° C.

8. The process according to claim 5 in which hydrobromic acid exceeds by 5-10% the calculated galanthamine content in the mixture.

9. The process according to claim 1 in which the aqueous basic solution is a basic aqueous solution at pH≧8 and the base is selected from sodium, potassium, calcium hydroxide or carbonate and ammonium hydroxide.

10. The process according to claim 1 in which the solvent of formula (II) is n-butyl acetate.

11. The process according to claim 1 further comprising the conversion of galanthamine into galanthamine hydrobromide.

12. The process as claimed in claim 11 in which the conversion into galanthamine hydrobromide is carried out without isolating galanthamine.

* * * * *